(12) United States Patent
Boyden et al.

(10) Patent No.: US 8,708,965 B2
(45) Date of Patent: Apr. 29, 2014

(54) SCALABLE PARALLEL GENE THERAPY INJECTOR ARRAY

(75) Inventors: Edward S. Boyden, Chestnut Hill, MA (US); Stephanie Chan, Hong Kong (HK)

(73) Assignee: Massachusetts Institute of Technology, Cambridge, MA (US)

( * ) Notice: Subject to any disclaimer, the term of this patent is extended or adjusted under 35 U.S.C. 154(b) by 167 days.

(21) Appl. No.: 12/619,685

(22) Filed: Nov. 17, 2009

(65) Prior Publication Data
US 2010/0152662 A1 Jun. 17, 2010

Related U.S. Application Data

(60) Provisional application No. 61/115,167, filed on Nov. 17, 2008.

(51) Int. Cl.
*A61M 5/00* (2006.01)
(52) U.S. Cl.
USPC ......... 604/173; 604/151; 604/93.01; 204/604

(58) Field of Classification Search
USPC .......... 604/46, 47, 131, 151, 173, 174, 93.01; 204/604
See application file for complete search history.

(56) References Cited

U.S. PATENT DOCUMENTS

| | | | | |
|---|---|---|---|---|
| 5,697,901 | A * | 12/1997 | Eriksson | 604/46 |
| 5,792,110 | A * | 8/1998 | Cunningham | 604/158 |
| 7,083,592 | B2 * | 8/2006 | Lastovich et al. | 604/47 |

* cited by examiner

*Primary Examiner* — Laura Bouchelle
(74) *Attorney, Agent, or Firm* — Norma E. Henderson

(57) ABSTRACT

A scalable parallel injector array has a support structure for holding injector tubes in a spatial pattern in order to enable delivery of fluidic materials simultaneously to a group of specific target areas in the brain or a body part. Each injector is individually connectible at one end to a displacement-controlled pump and is designed at the other end to be inserted into the brain or body part. The injector tubes are connected to the pump by fluid-filled tubing. The spatial pattern is patient- and/or application-customizable, and the length of the injector tubes is customizable in order to more precisely reach individual target areas. A clamping device may be used to attach the injector array to a stereotaxic arm or other support structure. The action of the pump permits controlled simultaneous delivery of the fluidic materials to the target areas.

16 Claims, 4 Drawing Sheets

SCALABLE PARALLEL GENE THERAPY INJECTOR ARRAY

RELATED APPLICATIONS

This application claims the benefit of U.S. Provisional Application Ser. No. 61/115,167, filed Nov. 17, 2008, the entire disclosure of which is herein incorporated by reference.

STATEMENT REGARDING FEDERALLY SPONSORED RESEARCH OR DEVELOPMENT

This invention was made with U.S. government support under Grant Number 1-DP2-OD002002-01, awarded by the National Institutes of Health (NIH). The government has certain rights in this invention.

FIELD OF THE TECHNOLOGY

The present invention relates to the field of gene therapy and, in particular, to devices for delivering therapeutic or other materials to target areas.

BACKGROUND

Gene therapy is a rapidly growing field, with the explosion being led by the proven safety and efficacy of adeno-associated viruses (AAV). AAV are common to nearly all (~95%) humans and have no side effects (such as the cancers associated with retroviruses) or toxic outcomes. They permanently deliver genes to cells, and have been used safely in over 600 patients in 48 separate clinical trials, without a single serious adverse event.

For example, it has recently been shown that viruses encoding for light-sensitive proteins can sensitize specific cell types to millisecond-timescale activation and silencing in the intact brain. A number of genetically-encoded optical sensitizers have enabled neurons to be activated and silenced in vivo in a temporally-precise fashion in response to brief pulses of light (e.g., B. Chow, X. Han, X. Qian, and E. S. Boyden, Frontiers in Systems Neuroscience. Conference Abstract: Computational and systems neuroscience. doi: 10.3389/conf-.neuro.10.2009.03.347 (2009); F. Zhang, L. P. Wang, M. Brauner, J. F. Liewald, K. Kay, N. Watzke, P. G. Wood, E. Bamberg, G. Nagel, A. Gottschalk, and K. Deisseroth, Nature 446 (7136), 633 (2007); E. S. Boyden, F. Zhang, E. Bamberg, G. Nagel, and K. Deisseroth, Nat Neurosci 8 (9), 1263 (2005); X. Han and E. S. Boyden, PLoS ONE 2 (3), e299 (2007); L. Luo, E. M. Callaway, and K. Svoboda, Neuron 57 (5), 634 (2008); S. Szobota, P. Gorostiza, F. Del Bene, C. Wyart, D. L. Fortin, K. D. Kolstad, O. Tulyathan, M. Volgraf, R. Numano, H. L. Aaron, E. K. Scott, R. H. Kramer, J. Flannery, H. Baier, D. Trauner, and E. Y. Isacoff, Neuron 54 (4), 535 (2007); S. Q. Lima and G. Miesenbock, Cell 121 (1), 141 (2005)). A key method by which neurons have been sensitized to light in the mammalian brain is via viruses such as AAV and lentiviruses, which can deliver genes encoding for opsins to brains of animals ranging from mice to monkeys, in a safe and enduring fashion (e.g., A. Bi, J. Cui, Y. P. Ma, E. Olshevskaya, M. Pu, A. M. Dizhoor, and Z. H. Pan, Neuron 50 (1), 23 (2006); X. Han, X. Qian, J. G. Bernstein, H.-H. Zhou, G. Talei Franzesi, P. Stern, R. T. Bronson, A. M. Graybiel, R. Desimone, and E. S. Boyden, Neuron 62 (2), 191 (2009); F. Zhang, L. P. Wang, E. S. Boyden, and K. Deisseroth, Nat Methods 3 (10), 785 (2006); T. Ishizuka, M. Kakuda, R. Araki, and H. Yawo, Neurosci Res 54 (2), 85 (2006)). Viruses allow faster turn-around time than do transgenics, especially for organisms that are not genetic model organisms such as rats and monkeys, and for opsins may enable high expression levels that may not be possible in transgenic scenarios [H. Wang, J. Peca, M. Matsuzaki, K. Matsuzaki, J. Noguchi, L. Qiu, D. Wang, F. Zhang, E. Boyden, K. Deisseroth, H. Kasai, W. C. Hall, G. Feng, and G. J. Augustine, Proc Natl Acad Sci USA 104 (19), 8143 (2007)].

Little work has been done on supporting hardware that would enable delivery of AAV vectors to multiple points in the brain. Gene therapy technologies are typically delivered to single points in the body or brain. However, injections of viruses or other gene therapy systems at single points can only label single points; increasing the volume of virus delivered is in principle possible, but is only marginally effective, and it is impossible to label cells in a complex spatial pattern (e.g., a flat disc, or a curved line) with a single-point injector. Furthermore, it is tedious, time-consuming, and error prone to perform such injections of viruses or gene therapy systems into the brain in series. For seizure silencing, or treating Parkinson's disease, or treating depression, it may be desirable to deliver genes to multiple points in a neural network, at several points along its path. Understanding how neural circuits mediate the computations that subserve sensation, thought, emotion, and action, and are corrupted in neurological and psychiatric disorders, would be greatly facilitated by a technology for rapidly targeting genes to complex 3-dimensional neural circuits, enabling fast creation of "circuit-level transgenics."

SUMMARY

Delivery of genes in complex spatial patterns, as may be required for the brain because of its complex geometry, requires a method for 3-D delivery of viruses or other gene therapy systems into a set of predetermined points, preferably in a patient-customized fashion. As disclosed herein, this may be accomplished using a displacement-controlled parallel injector system, consisting of an array of capillary tubes, whose distal ends terminate in an arbitrary 3-D pattern, and whose proximal ends are connected in parallel to a displacement-control pump. The invention provides supporting hardware that enables delivery of AAV vectors to multiple points in the brain, providing functionality such as the ability to label arrays of points in the brain with optical control molecules. It is designed to be an enabling technology, widely applicable to a variety of disorders.

An injector array according to the present invention is capable of delivering viruses or other fluids to dozens of defined points within the 3-dimensional structure of the brain. The injector array comprises one or more displacement pumps that each drive a set of syringes, each of which feeds into a polyimide/fused-silica capillary via a high-pressure-tolerant connector. The capillaries are sized, and then inserted into, desired locations specified by custom-milling a stereotactic positioning board, thus allowing viruses or other reagents to be delivered to the desired set of brain regions. To use the device, the surgeon first fills the fluidic subsystem entirely with oil, backfills the capillaries with the virus, inserts the device into the brain, and infuses reagents slowly. The parallel nature of the injector array facilitates rapid, accurate, and robust labeling of entire neural circuits with viral payloads such as optical sensitizers to enable light-activation and silencing of defined brain circuits. Along with other technologies, such as optical fiber arrays for light delivery to desired sets of brain regions, the invention is intended to be part of a toolbox that enables the systematic probing of causal neural functions in the intact brain. This technology may not only open up such systematic approaches to circuit-focused neuroscience in mammals, and facilitate labeling of brain regions in large animals such as non-human primates, but may also open up a clinical translational path for cell-specific optical control prosthetics, whose precision may improve the treatment of intractable brain disorders. Such devices may also facilitate precisely-timed fluidic delivery of other payloads, such as stem cells and pharmacological agents, to 3-dimensional structures, in an easily user-customizable fashion.

Thus, in one aspect the invention is an injector array comprising a support structure for holding a group of capillary tubes in a spatial pattern that permits delivery of fluidic materials in parallel to a plurality of specific target areas in the brain or a body part. Each capillary tube is individually connectible at one end to a displacement-controlled pump and adapted at the other end for insertion into the brain or body part for delivery of the fluidic materials. The capillary tubes may be connected to the displacement-controlled pump by means of tubing. The spatial pattern may be patient- and/or application-customizable. The number and length of the capillary tubes may be customizable.

In another aspect, the invention is an injector array system comprising a displacement-controlled pumping device, a group of tube injectors that are controllable by the displacement-controlled pumping device, with each tube injector being individually connected at one end to fluid-filled tubing connected to the displacement-controlled pumping device and adapted at the other end for insertion into a brain or body part to permit delivery of fluidic materials to the brain or body part, an injector array support structure for holding the group of tube injectors in parallel in a spatial pattern designed to permit simultaneous delivery of the fluidic materials to specific target areas in the brain or body part, and a clamping device for attaching the injector array support structure to a stereotaxic arm or other structure. The displacement-controlled pumping device may include a syringe connected to each tube injector via the tubing. The spatial pattern may be patient- and/or application-customizable. The number and length of the tube injectors may be customizable.

In a further aspect, the invention is a system adapted for delivery of fluidic materials to target areas of the brain or body, comprising a group of injectors, each injector being individually connectible at one end to a displacement-controlled pumping device and adapted at the other end for insertion into a brain or body part to permit delivery of fluidic materials to the brain or body part, each injector being controllable by the displacement-controlled pumping device, an injector array support structure for holding the injectors in parallel in a spatial pattern designed to permit simultaneous delivery of the fluidic materials to specific target areas in the brain or body part, and a clamping device for attaching the injector array support structure to a stereotaxic arm or other structure. Each injector may be connected to the pumping device by fluid-filled tubing. The pumping device may include a syringe associated with each connected injector, each syringe being connected to the associated injector via the tubing. The spatial pattern may be patient- and/or application-customizable. The number and length of the injectors may be customizable.

BRIEF DESCRIPTION OF THE DRAWINGS

Other aspects, advantages and novel features of the invention will become more apparent from the following detailed description of the invention when considered in conjunction with the accompanying drawings wherein.

DETAILED DESCRIPTION

The present invention is a parallel injector array capable of delivering viruses or other gene therapy systems to arbitrary sets of points distributed in a 3-dimensional fashion throughout the brain. Delivery of genes in complex spatial patterns, as is required for the brain with its complex geometry, and the variability of target positions from patient to patient, because of anatomical variability as well as disease target variability, requires a method for 3-D delivery of viral vectors or other gene therapy systems into a set of predetermined points. These problems are solved by a displacement-controlled parallel injector system, consisting of an array of capillary tubes, whose distal ends terminate in an arbitrary 3-D pattern, and whose proximal ends are connected in parallel to a displacement-controlled pump, which is not susceptible to the failure modes of a pressure-control pump. The injector array of the present invention provides the ability to label arrays of points in the brain with optical control or other molecules by providing a system for delivering a fluid to multiple sites distributed around a 3-D space. By injecting in parallel, this system accomplishes multi-target injections in much less time, and with less error, than serial injections. In addition, the injector array is accurate, easily customizable, reusable, and inexpensive. Altogether, these properties make it ideal for viral vector delivery into the brain. This system can also easily be used for the delivery of any fluid to any set of 3-dimensional coordinates.

Figure 1:
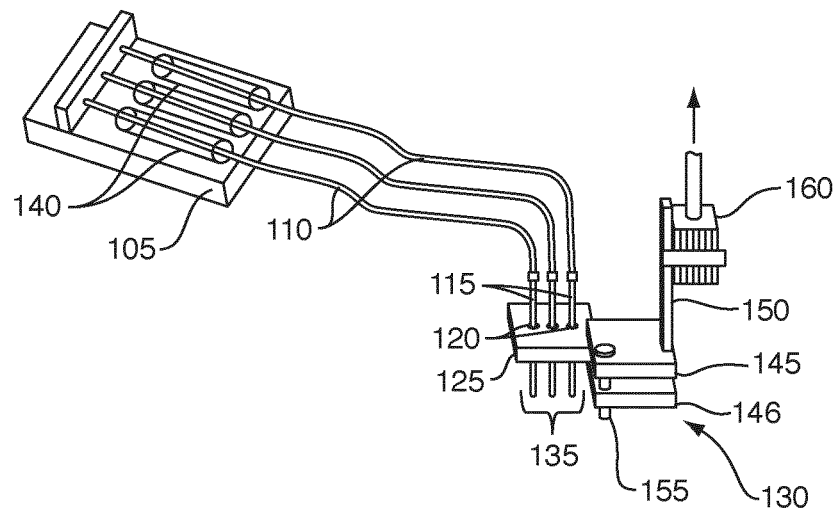
FIG. 1 is a schematic of an exemplary embodiment of an injector array having a three-injector configuration, according to one aspect of the present invention.

FIG. 1 is a schematic of an exemplary embodiment of an injector array having a three-injector configuration for three simultaneous injections, according to one aspect of the present invention. In FIG. 1, displacement-controlled pump 105 displaces oil in tubing 110 connected to thin capillaries or cannulas 115, which are custom specified to the patient and placed in a patient-customizable, custom-milled array of holes 120 in board 125. Board 125 is mounted in clamp 130 or other suitable holder for stereotaxic placement of the termini 135 of capillaries 115 into the brain or other body part. Displacement-controlled pump 105 includes one or more syringes 140 or equivalent pressure-containing manifolds, such as, but not limited to, an array of microfluidic channels. Syringes 140 are connected via stiff tubing 110, such as, but not limited to, polyethylene tubing, which connects to cannulas 115 inserted into custom-milled board 125 or any equivalent board with multiple holes positioned appropriately to target the desired regions within the brain or body.

Optionally, several boards can be stacked in order to provide additional support for the injectors. The width of the holes in the custom-milled board preferably matches the diameter of the capillary tubing, which is glued to the board. The cannulas are preferably held parallel to one another and terminate at different depths according to the depth of the targeted areas. For the exemplary demonstration device, the pump and syringes consisted of a Harvard Apparatus PHD-2000 pump holding 3 to 6 Hamilton syringes, which adjusts pressure in the line to suck in or push out fluid at the tip of the injectors. Such a single displacement-control pump can be used to control essentially an arbitrary number of injectors. The syringes, tubes, and injector cannulas were all filled with silicone oil, which is essentially incompressible and therefore accurate for the conveyance of pressure. While silicone oil was used in the exemplary device, it will be clear to one of skill in the art that any fluid with suitable characteristics may be advantageously used in the present invention.

The injectors themselves are preferably thin, in order to minimize damage to the brain, as well as to allow the close spacings necessary to infect a large, contiguous area. They must also be rigid enough that they maintain their precise shape and spacing under pressure, and so that they may be re-used, with lengths appropriate for their targets. It will be clear to one of skill in the art of the invention that many devices are available for use as the injectors of the invention, each with varying advantages and disadvantages. For example, although glass pipettes can be pulled so that they have thin, precise ends, they are fragile and their stems are wide. A better candidate is therefore thin capillary tubing made from fused silica. Steel is stronger, but causes more damage due to the thicker wall thickness. Each injector is attached to a single channel coming from the pump. Because the tips of the Hamilton syringes used in the exemplary demonstration device have much wider outer diameter than the inner diameter of the capillary tubing, intermediate tubing of the appropriate size was attached to the Hamilton syringes, and then connected to the much smaller capillary tubing using tubing sleeves, fittings, and ferrules, such as those available from Upchurch Scientific. It is preferable that the tubing used to connect to the Hamilton syringes be made of a non-flexible, oil-resistant material, because flexible tubing (e.g., silicone) may lead to inaccuracies by causing discrepancies between the pump displacement and the displacement of the silicone oil at the injector tip. Polyethylene has been shown to work well, but it will be clear to one of skill in the art that many other types of tubing would be suitable.

Board 125 and injectors 115 are attached to the stereotax with a clamp or other suitable holder that, in the exemplary device, consists of two pieces 145, 146 of laser-cut acrylic, although it will be clear to one of skill in the art of the invention that any sterilizable material could be used for this part. Pieces 145, 146 are glued together with hot glue on one edge, metal cannula 150 is epoxied perpendicularly through acrylic 145, 146, and tightening screw 155 is located in one of the non-glued corners. Metal cannula 150 of clamp 130 is attached to stereotax 160, as a glass pipette normally would be. Board 125 is placed between the two pieces of acrylic 145, 146 in one of the two remaining corners, and screw 155 is tightened so that board 125 is held firmly in place with respect to stereotax 160.

Figure 2:
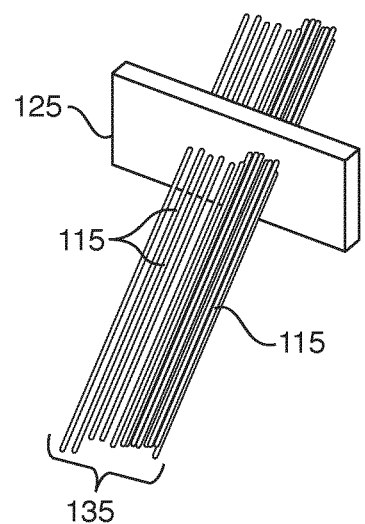
FIG. 2 is a depiction of an exemplary embodiment of a target-customized array, according to one aspect of the present invention.

FIG. 2 is a depiction of an exemplary embodiment of a target-customized array. Shown in FIG. 2 are multiple injectors 115 inserted through board 125. For a desired brain circuit, a mill is used to drill the holes through which the cannulas are inserted, thus forming the injectors. The injectors are reversibly mounted in the clamp, and then trimmed in order to accurately target the brain circuits of interest. As can be seen in FIG. 2, termini 135 of injectors 115 are of variable length in order to be able to reach the specific target areas of the brain. FIG. 2 also clearly illustrates that, while the exemplary embodiment of FIG. 1 depicts three injectors, any number of injectors may be present in the array of the present invention, depending on the particular application.

Virus injector arrays according to the present invention have been used in the laboratory to deliver viruses in a 3-D pattern, after which optical fibers have been inserted into those same sites to deliver light. Using the same board for both the virus injectors and fibers lends itself to delivering light to precisely the same regions that receive the virus. Preparation of the system for use involves filling the system (via the syringes) with silicone oil, and then loading fluidic reagents into the injectors. Fluidic reagents are initially loaded into the device by sucking up them into the tips of the cannulas by operating the displacement-controlled pump in reverse, without introducing air bubbles. Then the array is positioned with respect to the brain or other target organ using the stereotaxic arm, which can be positioned and give readings in three dimensions relative to a specified origin. The parallel injector array is then inserted into the brain targets, and the displacement-controlled pump effects, over a period of time, a displacement that slowly infuses the reagent payload into the brain.

Figure 3A:
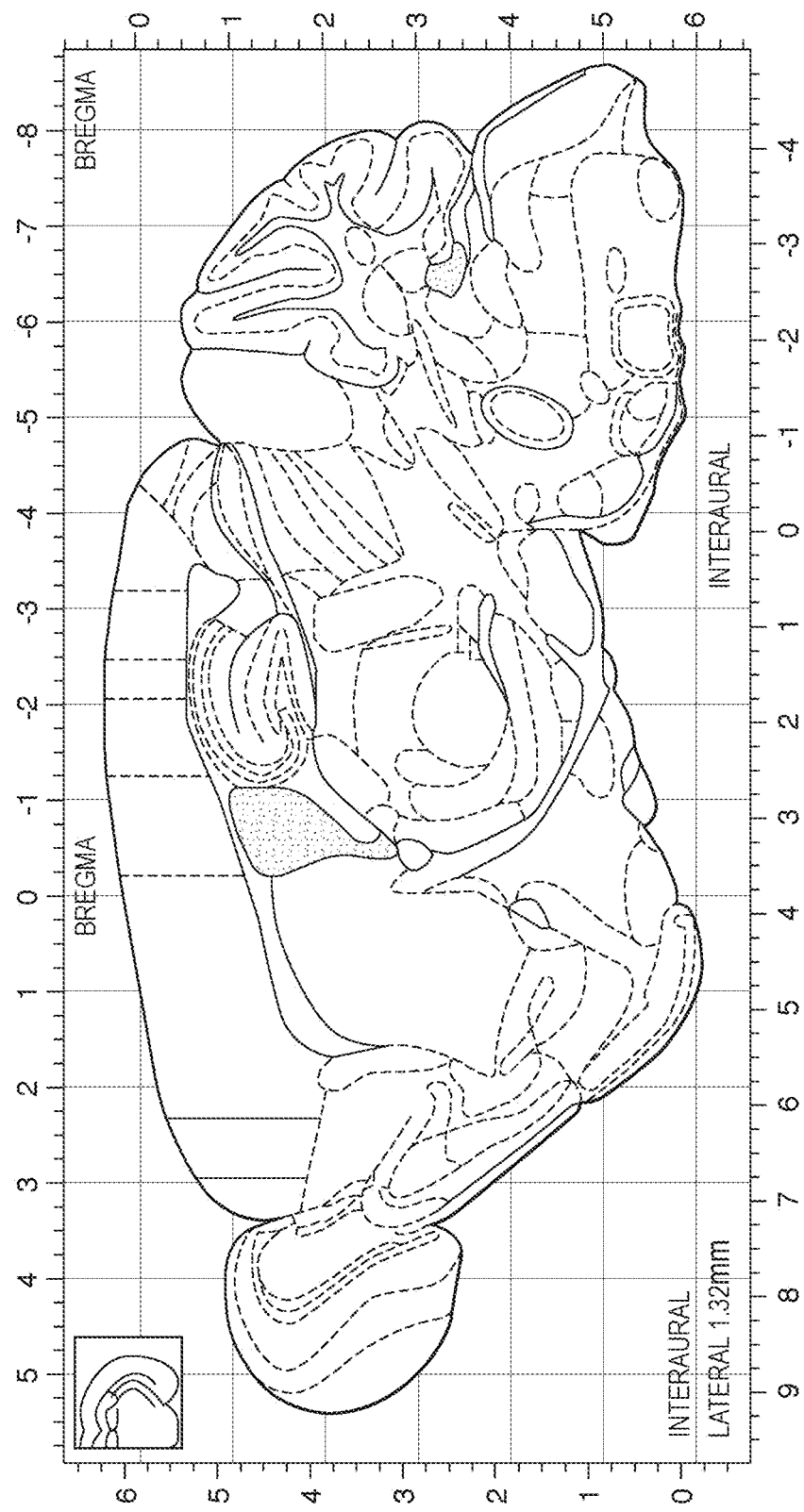
FIG. 3A is a schematic map of a mouse brain.
Figure 3B:
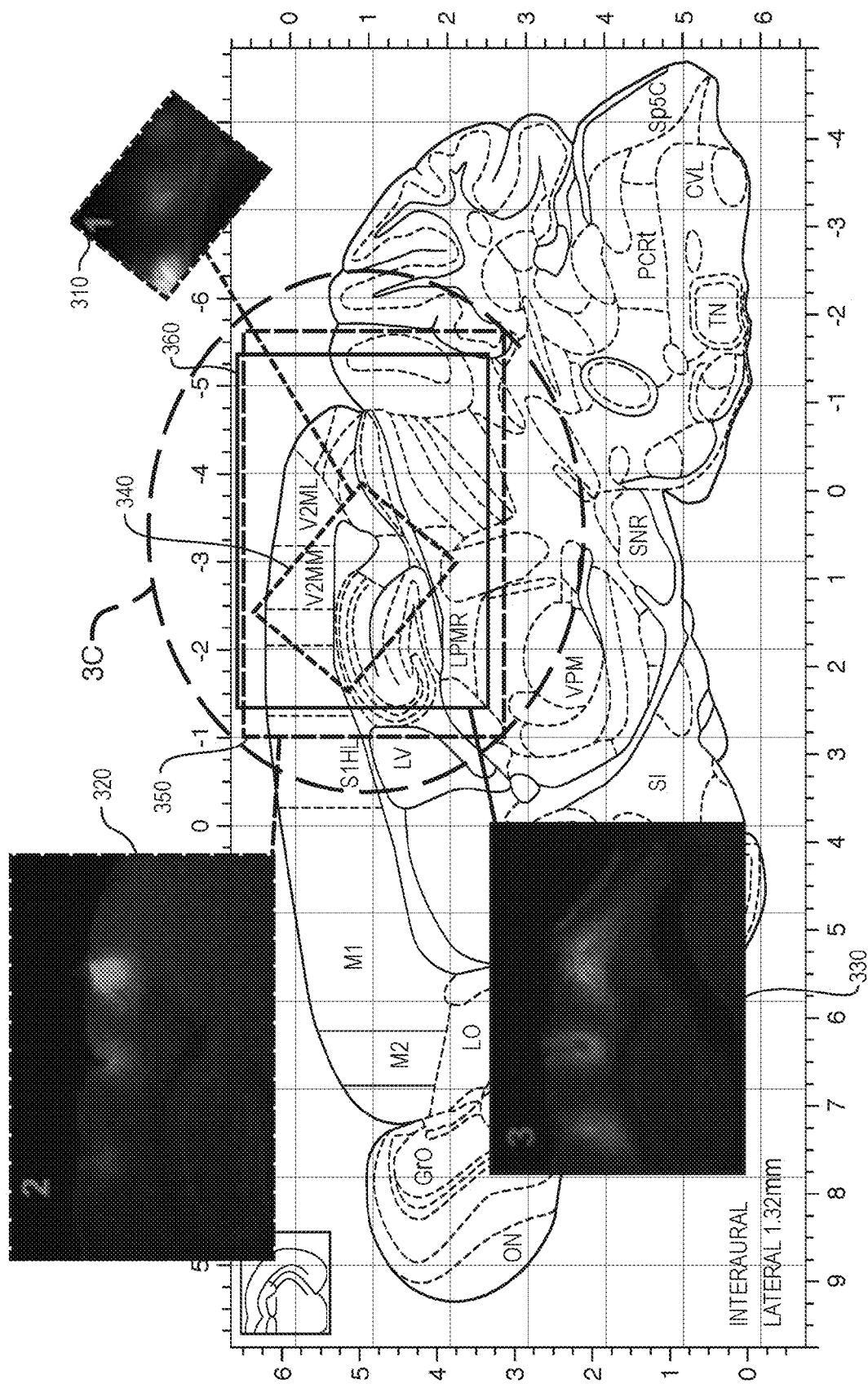
FIGS. 3B-C depict fluorescence images showing delivery of virus encoding for the gene ChR2-GFP into the mouse brain using a three-injector virus injector array according to the present invention, with an indication of the area covered by each fluorescence image being overlaid onto the schematic map of FIG. 3A and FIG. 3C being an enlargement of the inset shown in FIG. 3B.
Figure 3C:
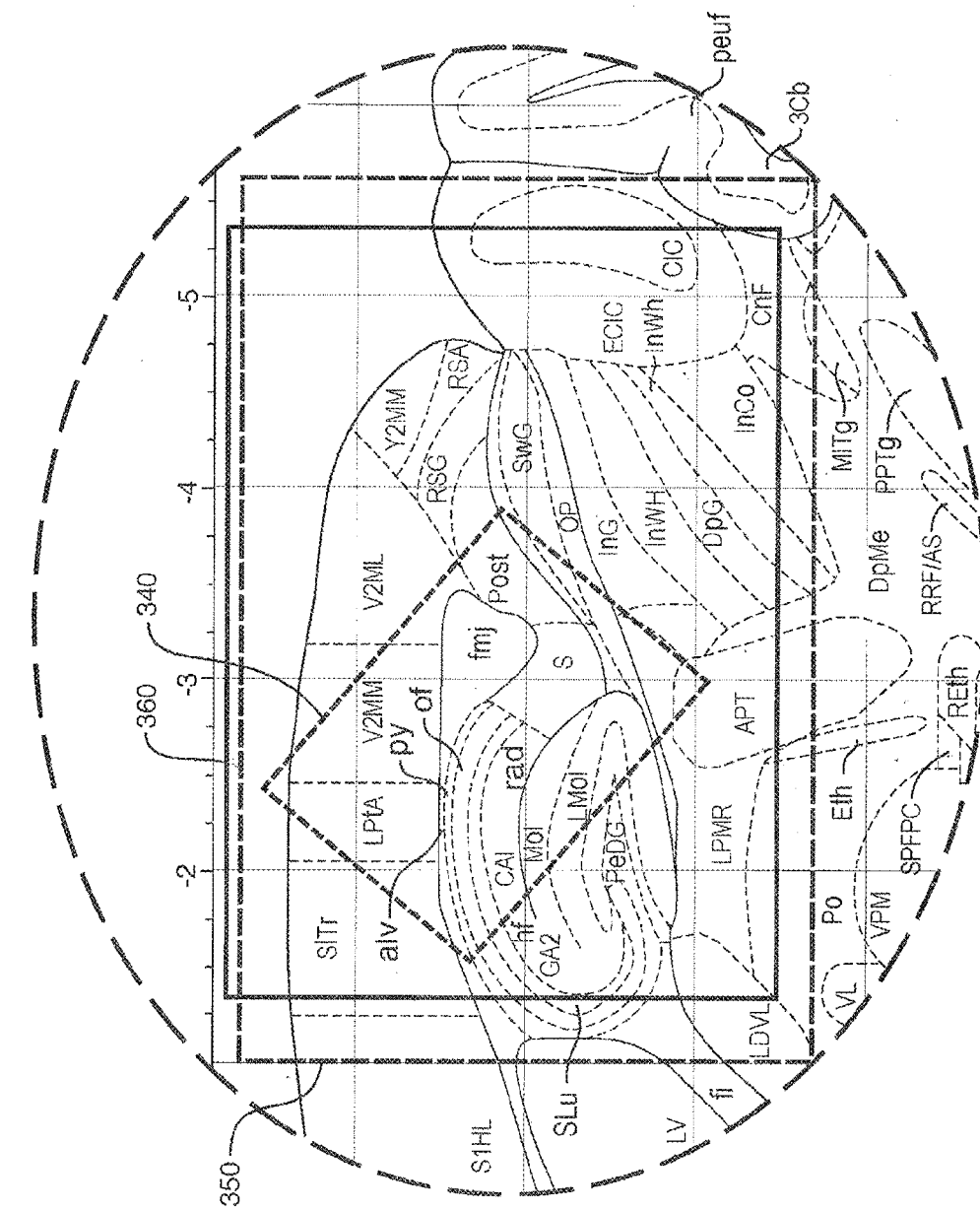

FIGS. 3A-C demonstrate how an array with three cannulas can be used to deliver gene therapy reagents to different parts of the mouse brain. FIG. 3A is a schematic map of a mouse brain and FIGS. 3B-C depict delivery of virus encoding for the gene ChR2-GFP into the mouse brain using a three-injector virus injector array according to the present invention. In FIGS. 3B-C, the specific area in the map of FIG. 3A that is covered by each fluorescence image 310, 320, 330 is shown as an overlay 340, 350, 360, respectively, on the schematic map. Fluorescence images 310, 320, 330 show ChR2-GFP-labeled cells in three mouse cortical regions, as targeted by the triple injector array, showing the ease of labeling multiple points in the brain with viruses using the injector array of the present invention. Each fluorescence image 310, 320, 330 shows a set of three volumes of labeled cells, which labeling was performed in a single step. It will be clear to one of skill in the art of the invention that displacement-controlled arrays according to the invention may be used for delivery of any small molecule to the brain.

Results from laboratory trials demonstrate that the parallel injector array of the invention speeds up a surgery roughly by a factor equal to the number of injectors, not counting setup and recovery time, although individual times will depend on the skill of the practitioner. For a 1-microliter injection, virus expression was typically seen in a sphere of approximately diameter 1 mm. The precision of the injection was such that the variability in tip positioning, from trial to trial, was about 45 microns (standard deviation of the distance from the tip position to the intended tip position).

Using the protocol and apparatus disclosed herein, it is possible to rapidly and precisely deliver a virus or other reagent to complex 3-dimensional patterns in the brain. The parallel injector array of the present invention is capable of creating, in a rapid timescale, "circuit-level transgenics", enabling entire 3-dimensional brain structures to be virally targeted with a gene, in a single surgical step. In addition to delivering viruses, the parallel injector array can deliver any fluidic reagent in the same manner to a complex distribution of brain sites, allowing, for example, dopaminergic agonists to be delivered in a patterned fashion to specific neural circuits in a headfixed behaving animal. For example, this array may be used to rapidly make circuit-specific transgenic mice, delivering viruses in parallel through the set of injectors to hit all the targets at once.

An exemplary experimental embodiment was constructed and used according to the methodology described below.

While an exemplary methodology for construction and use is described, it will be clear to one of skill in the art of the invention that many other methodologies of construction and use are equally suitable and will be considered within the scope of the invention. The exemplary methodologies are as follows:

Constructing the Stereotaxic Clamp. The stereotaxic clamp is used to attach the injector array to the stereotax in such a way that the injectors are parallel to the stereotaxic arm. In general, each lab needs the same number of clamps as the anticipated maximum number of simultaneous surgeries. It might also be advisable to make an extra, in case of damage to the first. To make the stereotaxic clamp, a 1.5 mm outer diameter (OD) steel cannula is cut to 2 inches in length, and one of the ends is Dremeled down until flat. Next, a small piece (approximately 0.5×0.5 cm) is cut out of PCB proto-board, to be used as a spacer. Using a laser cutter to ensure that any cuts made are perpendicular to the surface of the material, two identical rectangles (½"×⅜") are cut from ⅛" acrylic sheeting, each rectangle having two circular holes in opposite corners of the rectangle. The first hole has diameter 1.5 mm, and is just large enough to hold the metal cannula tightly. The second hole has diameter 1/16". The metal cannula is inserted into the 1.5 mm hole of one rectangle, then through the 1.5 mm hole of the second. The bottom end of the cannula is aligned with the bottom face of the bottom rectangle, forming the shape of a hockey stick. While keeping the spacer tightly held between the two rectangles, this structure is cemented together by using hot glue around the cannula and 1.5 mm holes, being careful to avoid gluing the spacer to the rectangles. Modeling clay may be helpful to hold things together during this process. After the glue has dried, a 1-72 hex nut can be attached to hold the clamp together as follows. Small amounts of 5-minute epoxy are dropped around the edge of the 1/16" hole. Then the hex nut is centered over the hole and placed firmly into the epoxy, without allowing the epoxy to get into the threads of the hex nut. Once the epoxy has hardened, a 1-72 binding slotted machine screw is inserted into the 1/16" hole from the top side of the rectangles, and screwed into the nut. Any modeling clay is removed, and it is confirmed that the spacer can be held firmly in place by tightening the screw.

Preparing the system for the customized injector array: Hamilton pump and stereotax. The injector array system can be customized to virtually any set of coordinates in the brain. The user first locates coordinates of desired injection sites in a mouse (or other species) brain atlas, converting to the appropriate coordinates used by the stereotax (here, X-, Y-, and Z-coordinates). The number of injection sites will hereafter be called k. k number of 10 µl Hamilton syringes are placed in an injection/withdrawal syringe pump such as this one from Harvard apparatus. Next, 3-foot-long pieces of polyethylene tubing are securely attached to the needle of each Hamilton syringe. For each piece of polyethylene tubing, an F-252 tubing sleeve from Upchurch Scientific is slid over the open end and attached to a P-627 tubing adapter using the included nut and ferrule, also from Upchurch Scientific.

Constructing the Customized Injector Array. Each injector array is customized to the set of coordinates that the user chooses. However, for sets of coordinates that differ only by a translation and/or rotation, the same injector array can be used. Considering only the relative X and Y coordinates of the injection sites, k holes are drilled into a PCB proto-board of thickness 1/32", with the same relative spacings. These holes are drilled using a Modela mini mill and a 0.011" diameter drill bit from Mcmaster-Carr. It is preferable to use a slow rate of drilling (Z-speed) to avoid breaking or wearing out the drill bit. Before removing the board from the mill, a rectangle is drilled around the small holes, using a larger drill bit of diameter 1/32", to avoid wearing out the smaller one. Code for the mini mill can be generated easily using MATLAB; sample code is provided in the following files: generate.m—MATLAB code for generating Modela code from desired coordinates, holes_ex.rml—Modela code for drilling ring pattern (eight holes) into Proto-board, and outline_ex.rml—Modela code for drilling rectangle around holes. 245 µm OD/100 µm inner diameter (ID) fused silica capillary tubing, available from Polymicro Technologies, is cut into k number of 3 inch pieces. These comprise the individual injectors. A discardable piece of capillary tubing is poked through each of the holes, to clear away debris without clogging the actual injectors. The injectors are then inserted halfway into each hole, so that they are held tightly and parallel to one another. The injectors are epoxied to the board, forming the structure of the injector array. All that remains is to trim the injectors to the correct length.

The injector array is attached to the stereotaxic clamp by placing one corner of the proto-board between the acrylic rectangles, and then by tightening the screw of the stereotaxic clamp. Next, the metal cannula of the clamp is attached to the stereotax, using the attachment mechanism of the stereotax. All of the following is done under a microscope: For one of the outer injectors (that is, one that can be approached from the side with a straight edge, without bumping into any of the other injectors), the tip extending beyond the bottom of the proto-board is cut with scissors. For cortical injections, it is appropriate to have the injector extending approximately 5 mm beyond the surface of the proto-board. For deeper injections, this number can be increased by the corresponding increase in depth. The tip is flattened with a Dremel tool. Injector tips can also be ground at an angle as an extra precaution against clogging, if precision in depth is less important. Next, a stable reference point is chosen within range of the stereotaxic arm, and the injector array is moved so that the flattened tip of the outer injector, is at this reference point. A second injector is chosen, along with its corresponding coordinates. Considered is the relative difference in height (z-direction) between the first and second injector coordinates. The injector array is moved along the Z-axis by this relative distance. The second injector is trimmed and Dremeled to the correct length, so that the tip of the second injector is now flat and at the height of the reference point. The injector array can be moved in the X- and Y-directions to facilitate comparison of the injector tip with the reference point. This process of trimming is repeated for the remaining injectors.

Assembling the entire system. The stereotaxic clamp and customized injector array, both already constructed, are required for this part. The back end of each injector (the end that has not been trimmed) is inserted into a blue F-240 tubing sleeve and, using a P-235 nut and P-200 ferrule from Upchurch Scientific, is attached to the threaded adaptor already connected to the Hamilton pump by polyethylene tubing. Manufacturer's instructions can be consulted for details. Using a 27-gauge needle, silicone oil is injected into the back of the Hamilton syringes so that the entire system is filled from the Hamilton syringe to the injector tip, with no air bubbles at all. As the Hamilton syringes are re-placed in the Hamilton pump, the greatest possible volume of silicone oil is maintained in the syringes. If the experiment requires more syringes than the pump is designed for (two in this case), the syringes can be spaced with small pieces of plastic (e.g., needle caps) to keep them parallel to one another, and to insure that all pieces are pushed by the pump to the same extent.

Detailed protocol for use. Attach the stereotaxic clamp to the stereotaxic device. Attach the customized PCB, containing the aligned cannulas, to the clamp, and screw in tightly. Make sure that all syringes, tubing, and cannulas are filled with silicone oil, with no air bubbles. Align the cannulas to the skull, the specific protocol for which will depend on the precise stereotax used. Rest the injector tips on a clean piece of Parafilm or other nonporous material. Pipette or otherwise deposit equal amounts of virus onto the end of each injector tip, or onto the Parafilm. If the injection sites are at widely differing depths, raise small pieces of Parafilm to different heights, or sculpt/print an appropriately shaped plastic piece. Fill the injectors with slightly more virus than required, then lower the injectors to the desired injection sites in the brain, and inject at low speeds (~0.1 uL/min). When finished, wait 10-20 minutes, and then be sure to withdraw the array at a slow rate.

Injections/surgery. The process of injecting with a parallel injector is very similar to that of injecting with a single pipette. It is best to use slow refill/infuse rates throughout this process, because fast pumping may put stress on the joint between the large and small tubing. Recommended max rate: 2 µl/min for loading virus, and 0.1 µl/min for infusing virus. An anesthetized mouse is placed in the stereotax, and remains anesthetized throughout the experiment. Prepare the mouse as needed. For example, with a scalpel, a single cut is made down the midline of the skin, from between the eyes to between the ears. The skin is pulled back to expose the skull, and the fascia is cleaned off. A pulled glass pipette is attached to the stereotax. The positions of the ear bars are adjusted until bregma and lambda are aligned to the same height, and so that the line connecting them is parallel to the Y-axis of the stereotax. The axes of the stereotax are oriented according to the coordinate system in which the injection coordinates have been calculated. The stereotaxic is zeroed with the tip of the glass pipette at bregma, and then the tip is positioned slightly above the skull at the X- and Y-coordinates of one of the injection sites.

One technique for efficient, damage-minimizing, opening of holes in skull for injector insertion into brain: with a dental drill, thin the skull down to ~50 microns thickness, then use the tip of a sharp needle to open a small craniotomy. Using a dental drill, the skull below the tip is carefully pared away until there remains an extremely thin layer of bone. The glass pipette can be lowered and raised to check that the hole being drilled is centered at the correct position. Using a 30-gauge needle, a tiny piece of the layer is gently picked off, at the correct X- and Y-coordinates, so that the dura mater is exposed. This hole should be just large enough to fit one of the injectors (0.25 mm wide). In this way, small, 0.25 mm wide holes are made in the skull, at the X- and Y-coordinates corresponding to each injection site. Then screws are inserted into the skull, as required for the implantation of an LED-fiber array. The holes made previously will be used for the LED-fiber array as well. The glass pipette is discarded in a sharps container, and the customized injector array is attached to the stereotax using the stereotaxic clamp.

In order to correctly set the angle of the injector array, two outer injectors are chosen to be calibrated to a given reference point, as follows. After one of the injectors is matched with the reference point, consider the relative X- and Y-distances between the injection sites relative to this injector and one other. The axes of the stereotax are adjusted so that entire injector array is moved in the X- and Y-directions by these relative distances. If the second injector is not now aligned with the reference point, the metal cannula is loosened and rotated. This process is repeated iteratively until the injector array is angled correctly. Before filling the injectors with virus, the injectors are filled with silicone oil until the syringes are at the 2 µl point (or greater). This provides a buffer zone, so that any air bubbles or clogging in the tip can be easily removed by pushing oil forward using the Hamilton pump, without having to refill the entire system with silicone oil from the back of the syringes, as describe previously. A clean piece of Parafilm is placed on the skull, and the injectors are gently lowered onto the Parafilm. For coordinates with greatly varying depths, a custom-milled part (e.g. a staircase-shaped object) could facilitate loading.

The following parts assume that 1 ml of virus is to be loaded at each site. The quantities should be scaled down if smaller quantities are desired. In order to guarantee that >1 µl of virus is injected at each site, 1.5 µl of virus is pipetted onto the Parafilm or staircase at the tip of each injector. With the refill rate of the Hamilton pump set to 1 µl/min, 1.2 µl of the virus is refilled into each injector. The tip of the longest injector is zeroed at bregma, and then the injector array is shifted to the X- and Y-coordinates of that injector. If clogging is an issue, for example if many deep targets are involve: even before inserting the injector tips into the brain, it is sometimes advisable to start the pump infusing until virus can be seen emerging from all the injector tips. This removes any air bubbles at the injector tips, and also ensures that there is no clogging. In the case of clogging, the Hamilton pump is set to infuse a brief pulse at a higher speed of 2 µl/min, to blast out any clogging. The injector array is then lowered, through the small holes made with the 30-gauge needles, to the correct Z-depth. 1 ml of virus is injected through each injector, at 0.1 µl/min. The injections are left alone for 30 minutes. After the injector array is slowly extracted from the brain, the Hamilton pump is set to infuse at the same rate of 0.1 ml/min, in order to check for clogging in each injector. Then the injectors are cleaned by refilling and infusing 1.5 µl of ethanol at 2 µl/min. Finally, the injectors are refilled with silicone oil to maintain the 2 ml buffer zone in each Hamilton syringe. The LED-fiber array can now be implanted.

Parallel injector arrays according to the present invention may be used to inject almost any payload, for example, but not limited to, drugs, neuromodulators, neurotransmitters, or cells, in complex 3-D patterns in the brain, in a temporally-precise manner. From a translational standpoint, it is possible that rapid, patient-customized gene therapy or drug delivery devices may be rapidly custom-designed and fabricated to match individual brain geometries, supporting new treatments for a variety of pathologies, potentially through the use of optical control molecules. The injector arrays of the invention are designed to be precise, both spatially and volumetrically. In the X- and Y-directions, this is accomplished by drilling very accurately placed holes using an inexpensive mini-mill, with the holes just large enough to fit the injectors, so that injectors are held parallel to one another, and in a precise location. In the Z-direction, the injectors are trimmed using a stereotaxic apparatus, allowing a level of precision equivalent to that of the stereotaxic surgery itself. The volumetric precision arises from the precision of the Hamilton pump, as well as the near-zero dead-volume connectors, adapted from the high-pressure liquid chromatography (HPLC) field. The injectors are made from fused silica capillary tubing, which is strong and rigid enough that it maintains precise shape and spacing under pressure, without the larger wall thickness of alternatives such as steel cannulas. Small modifications can easily be made to adapt the parallel injector array to a variety of experiments. For example, if smaller volumes of virus or finer spacings are required, smaller capillary tubing can be employed, along with a corresponding smaller drill bit. Future devices may utilize microfluidic channels and pumps, to increase the number of parallel injectors, to minimize the size (perhaps enabling such devices to be mounted on the heads of freely-moving animals).

This technology will enable a wide variety of new kinds of experiments, such as millisecond-timescale shutdown of complexly-shaped structures (such as the hippocampus) at precise times during behavior, temporally-precise inactivation of bilateral structures that may act redundantly (such as the left and right amygdala), and the perturbation of multiple discrete brain regions (e.g., driving two connected regions out of phase to study how cross-region synchrony depends upon activity within each region, or stimulating inputs to a region while silencing a subset of the targets in order to understand which of the several targets are critical for mediating the effects of those inputs). For large brains like those in the primate, in which optical cell-type specific neural activation has been recently demonstrated [X. Han, X. Qian, J. Bernstein, H.-H. Zhou, G. Talei Franzesi, Stern P., R. T. Bronson, A. Graybiel, R. Desimone, and E. S. Boyden, in press, Neuron (2009)], perturbing activity in a behaviorally-relevant area may require viral labeling of large, complex structures. Along with other technologies, such as optical fiber arrays for light delivery to desired sets of brain regions, it is hoped to create a toolbox that enables the systematic probing of causal neural functions in the intact brain.

While a preferred embodiment is disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

What is claimed is:

1. An injector array, comprising:
a plurality of capillary tubes of varying lengths, each capillary tube being individually connectible at a proximal end to a displacement-controlled pump, each capillary tube being adapted at a distal end for insertion into a brain or body part, each capillary tube being further adapted for delivery of fluidic materials through the distal end to the brain or body part, wherein the length of each individual capillary tube is individually determined according to the location of a respective one of a plurality of specific target areas in the brain or body part and at least some of the individual capillary tubes are of different lengths than others of the individual capillary tubes;
a support structure for holding the plurality of capillary tubes such that their distal ends, taken together, terminate in a three-dimensional spatial pattern that permits delivery of the fluidic materials in parallel to the plurality of specific target areas in the brain or body part; and
a stereotaxic device to which the support structure is attachable, the stereotaxic device being configured to control the angular orientation of the support structure with respect to the brain or body part so that the distal end of each capillary tube is positioned at its respective target area.

2. The injector array of claim 1, wherein the capillary tubes are connectible to the displacement-controlled pump by means of tubing.

3. The injector array of claim 1, wherein the spatial pattern is patient-customizable.

4. The injector array of claim 1, wherein the number of capillary tubes is customizable.

5. The injector array of claim 1, wherein the support structure is a custom-milled board through which the capillary tubes pass.

6. An injector array system, comprising:
a displacement-controlled pumping device;
a plurality of tube injectors of varying lengths, each tube injector being individually connected at a proximal end to fluid-filled tubing connected to the displacement-controlled pumping device, each tube injector being adapted at a distal end for insertion into a brain or body part to permit delivery of fluidic materials through the distal end to the brain or body part, each tube injector being controllable by the displacement-controlled pumping device, wherein the length of each individual tube injector is individually determined according to the location of a respective one of a plurality of specific target areas in the brain or body part and at least some of the individual tube injectors are of different lengths than others of the individual tube injectors;
an injector array support structure for holding the plurality of tube injectors in parallel such that their distal ends, taken together, terminate in a three-dimensional spatial pattern designed to permit simultaneous delivery of the fluidic materials to the specific target areas in the brain or body part;
a stereotaxic device to which the support structure is attachable, the stereotaxic device being configured to control the angular orientation of the support structure with respect to the brain or body part so that the distal end of each tube injector is positioned at its respective target area; and
a clamping device for attaching the injector array support structure to the stereotaxic device.

7. The injector array system of claim 6, the displacement-controlled pumping device further comprising a syringe associated with each connected tube injector, each syringe being connected to the associated tube injector via the tubing.

8. The injector array system of claim 6, wherein the spatial pattern is at least one of patient-customizable or application-customizable.

9. The injector array system of claim 6, wherein the number of tube injectors is customizable.

10. The injector array system of claim 6, wherein the support structure is a custom-milled board through which the tube injectors pass.

11. A system adapted for delivery of fluidic materials to target areas of the brain or body, comprising:
a plurality of injectors of varying lengths, each injector being individually connectible at a proximal end to a displacement-controlled pumping device, each injector being adapted at a distal end for insertion into a brain or body part to permit delivery of fluidic materials through the distal end to the brain or body part, each injector being controllable by the displacement-controlled pumping device, wherein the length of each individual injector is individually determined according to the location of a respective one of a plurality of specific target areas in the brain or body part and at least some of the individual injectors are of different lengths than others of the individual injectors;

an injector array support structure for holding the plurality of injectors in parallel such that their distal ends, taken together, terminate in a three-dimensional spatial pattern designed to permit simultaneous delivery of the fluidic materials to the specific target areas in the brain or body part; and a stereotaxic device for attaching to the injector array support structure, the stereotaxic device being configured to control the angular orientation of the support structure with respect to the brain or body part so that the distal end of each injector is positioned at its respective target area.

12. The system of claim 11, further comprising fluid-filled tubing connecting each injector to the pumping device.

13. The system of claim 12, further comprising the displacement-controlled pumping device, the pumping device further comprising a syringe associated with each connected injector, each syringe being connected to the associated injector via the tubing.

14. The system of claim 11, wherein the spatial pattern is at least one of patient-customizable or application-customizable.

15. The system of claim 11, wherein the number of injectors is customizable.

16. The system of claim 11, wherein the support structure is a custom-milled board through which the injectors pass.

* * * * *